United States Patent [19]
Sekiguchi et al.

[11] Patent Number: 4,869,787
[45] Date of Patent: Sep. 26, 1989

[54] ELECTROCHEMICAL METHOD FOR DETERMINING END POINTS OF ORGANIC OR INORGANIC REACTIONS

[75] Inventors: Tadao Sekiguchi, Wakayama; Utaji Sawa, Nara; Kazunori Wada, Osaka, all of Japan

[73] Assignee: Sumitomo Chemical Company, Ltd., Osaka, Japan

[21] Appl. No.: 183,292

[22] Filed: Apr. 11, 1988

Related U.S. Application Data

[63] Continuation-in-part of Ser. No. 32,926, Mar. 30, 1987, abandoned, which is a continuation of Ser. No. 819,653, Dec. 17, 1985, abandoned.

[30] Foreign Application Priority Data

Dec. 19, 1984 [JP] Japan .................................. 59-268052

[51] Int. Cl.⁴ ...................... G01N 27/30; G01N 27/52
[52] U.S. Cl. ..................................... 204/1 T; 204/400
[58] Field of Search ............. 204/400, 1 K, 1 M, 1 N, 204/1 T

[56] References Cited

U.S. PATENT DOCUMENTS

| | | | |
|---|---|---|---|
| 4,409,183 | 10/1983 | Fischer | 422/68 |
| 4,457,808 | 7/1984 | Taylor | 204/1 T |
| 4,543,175 | 9/1985 | Subsara et al. | 204/400 |
| 4,582,572 | 4/1986 | Ishikawa | 204/1 T |
| 4,783,250 | 11/1988 | Pons et al. | 204/400 |

Primary Examiner—G. L. Kaplan
Attorney, Agent, or Firm—Jones, Tullar & Cooper

[57] ABSTRACT

Herein disclosed are an electrochemical method for determining the end point of oxidation-reduction reactions, certain exchange reactions or precipitation reactions of organic or inorganic compounds and a dipole gold electrode used therein. The method comprises immersing a pair of electrodes or an electrode having a gold sensing portion and detecting and analyzing variations in electrical potential or current observed during the reaction. The electrode comprises a tube having a closed bottom, a pair of gold members passed through and projected outside the tube, a pair of terminals disposed at the top of the tube and a pair of metal elements electrically connecting the gold members and the terminals. This method and the electrode makes it possible to effectively determine the end point of the reaction with high accuracy and good reproducibility.

7 Claims, 7 Drawing Sheets starting material monoazo compound excess diazo component

ELECTROCHEMICAL METHOD FOR DETERMINING END POINTS OF ORGANIC OR INORGANIC REACTIONS

This is a continuation-in-part of application Ser. No. 032,926 filed Mar. 30, 1987 which in turn was a continution of application Ser. No. 819,653 filed Dec. 17, 1985, both now abandoned.

BACKGROUND OF THE INVENTION

1. Field of the Invention

The present invention relates to an electrochemical method for determining the end point of organic or inorganic reactions and an electrode used in the method. More particularly, the invention pertains to a method for electrochemically detecting the end point or monitoring the status of an organic reaction, and in particular diazotization, or azo coupling reactions or other organic or inorganic reactions, in which an oxidation-reduction reaction, an exchange reaction or a precipitation reaction takes place, by utilizing potentiometric or amperometric techniques, and to a gold electrode effective to carry out the method.

2. Description of the Prior Art

It is quite important to precisely detect the end point of an oxidation-reduction reaction of organic compounds or inorganic compounds or the like, in order to improve the quality of the products resulting therefrom, and to make the reaction more economical.

For instance, among dyestuffs, azo dyestuffs having azo groups (—N=N—) as the chromophore may be used as the starting material for deriving various kinds of other dyestuffs by combining them with other chromophores or auxochromes. The azo dyestuff makes it possible to obtain dyestuffs belonging to acid dyestuffs, direct dyestuffs, basic dyestuffs, mordant dyestuffs, insoluble azo dyestuffs and pigments. In light of their dyeing ability and the color tone of these dyestuffs, derived from azo dyestuff, almost their whole range is extended. At least a third of the dyestuffs presently on the market fall within this kind of dyestuff, since these can relatively economically and easily be prepared by combining diazotization and azo coupling reactions.

In the diazo coupling reaction, hydrochloric acid is generally used and, in particular, it should be used in a large amount if the reaction is carried out under the condition such that a diazoamino compound may easily be formed in the reaction system. Moreover, the diazonium salt formed during the diazotization reaction is relatively unstable and therefore, the subsequent coupling reaction may be impaired by the excess nitrous acid which may still be present after the diazotization reaction. In such a case, one must pay careful attention to the reaction so as to check the presence of nitrous acid and the nitrous acid possibly present must be decomposed by sulfamic acid ($H_2NSO_3H$) or urea ($H_2NCONH_2$) prior to subsequent reactions. If such careful attention is not paid, the quality of the product becomes quite low. In order to eliminate the detrimental effects mentioned above, therefore, it is necessary to correctly detect the end point of the reaction concerned, exactly estimate the amount of excess nitrous acid at that time and eliminate it before recovering and storing the resulting product. Therefore, there is a great need for developing a technique for detecting an exact end point and estimating an exact amount of residual nitrous acid present in the reaction system.

It is also important to monitor the status of reactions at each desired stage during the reaction. For example, in the case of diazo dyestuff synthesis, it is known that the secondary coupling reaction is started immediately after the completion of the primary coupling reaction. However, if one wants to recover the product of the primary coupling reaction, it is necessary to find conditions therefor by monitoring the reaction process exactly. In addition, monitoring of the reaction process is effective to estimate and control the rate of reaction.

Conventionally, as the method for monitoring reaction processes and detecting the end point of a diazotization reaction or an azo coupling reaction, there is known, for example, a method which comprises detecting the presence of excess nitrous acid by examining the coloration of potassium iodide-starch paper as the external indicator (see, for example, JIS K4101 11, 3-3, 1980), in the case of diazotization, and a method which comprises effecting color reaction on a filter paper and estimating the extent of reaction from the color developed in the case of an azo coupling reaction (see JIS K4101 11, 2-1).

However, in these conventional methods, an operator must judge the extent of the reaction or the end point of the reaction according to his own visual color judgment and thus, the judgment would not be a complete one. In addition, such visual estimation requires well experienced personnel.

Under these circumstances, there has been proposed an electrochemical method for monitoring reaction processes and determining the end point thereof, and, as a typical technique there may be mentioned a method such as a polarographic method. The polarographic method comprises, for example, applying a potential, which linearly increases with time, to a sample to be examined and analyzing the observed electrical current variation with time. In the method, a dropping mercury electrode and a counter electrode of mercury pool having a large electrode surface are generally used for an aqueous solution system.

As the method for detecting the end point and monitoring processes of diazotization or diazo coupling reactions according to the polarography technique, a method comprising observing and analyzing an electrical current variation due to the electrolysis of a diazo or azo compound formed during the reactions (see, Japanese Patent Publication No. 28719/73); a method using electrodes in which the sensing portion thereof is composed of platinum (JIS K4101 11, 2-1) and a method using a pair of electrodes, each of which has the sensing portion composed of a member selected from the group consisting of graphite, carbon, platinum or the like have been reported (see, for example, "Analysis method of K acid" issued by Bayer A. G., 1980).

However, there are many problems encountered in carrying out these conventional methods for electrochemically detecting the end point and processes of the reaction concerned, such that an apparatus provided with an electrolytic mechanism such as a dropping mercury electrode which is essential in the polarography technique, is necessary. And, if the electrochemical property of an amino group, a phenolic hydroxyl, an active methyline or a diazo group which takes part in the objective reaction is quite low, and an electrode of graphite, carbon, or platinum or a combination thereof is adopted, it is often observed that there is no detectable response such as a variation of the electrical potential or current. In particular, the reduction in sensitivity due to the contamination of the electrode surface makes the accuracy of the measurement quite low and constitutes an inherent disadvantage of the electrochemical method and apparatus, when monitoring the processes of a series of reactions without replacing the electrodes used.

Furthermore, in determining the end point of a coupling reaction, the following spot test is generally adopted, which comprises collecting a sample during the coupling reaction, dropping the sample on a filter paper to form a colorless moistured area, contacting a diazo solution with a part of the colorless area and an H-acid solution (indicator) with the other part of the colorless area (JIS K4101 11, 3-3, 1980). However, the spot test is believed to be effective only to determine the end point of a monoazo coupling reaction and is useless in determining the end point of the reaction in which at least two coupling reactions successively take place such as diazotization and trisazotization reactions. In such a case, the end point is indirectly determined by detecting the unreacted monoazo component according to a liquid chromatography technique or the like.

In the light of the aforementioned situation of the method for detecting the end point and monitoring the processes of an organic or inorganic reaction, it is industrially quite important to develop a new technique capable of solving the problems encountered in the conventional method in order to accurately detect the end point, to make the electrochemical analysis of various kinds of reactions and the process control thereof easier and to obtain an objective product more economically and effectively.

SUMMARY

A principal object of this invention is to provide an electrochemical method for detecting the end point of oxidation-reduction reaction, an exchange reaction or precipitation reactions of organic compounds or inorganic compounds or monitoring the process of the reaction in a high accuracy.

Another objects of this invention is to provide an electrochemical method for determining the end point of reactions, in which at least two coupling reactions successively take place, such as diazotization and trisazotization, the end point of which it indirectly determined conventionally.

A further object of this invention is to provide an electrochemical method for exactly detecting or monitoring the end point and processes of a reaction even when a functional group taking part in the reaction has a low electrochemical property such as a decomposition voltage.

A still further object of this invention is to provide an electrode which permits effectively carrying out the aforementioned method and to attain an exact measurement or monitor of the end point and processes of a reaction.

A further object of this invention is to provide an electrode which is not contaminated by adsorbing any components present in the solution examined or an electrode capable of maintaining a desired sensitivity even if the surface thereof is possibly contaminated with the component.

Accordingly, from studies on methods for electrochemically detecting or monitoring the end point and processes of organic or inorganic reactions a new method has been developed permitting the elimination of the disadvantages of the conventional methods explained above. The new method is quite effective in solving the problems accompanying the conventional methods by adopting a potentiometric titration or amperometric titration technique which utilizes gold, which is 99.0%, preferably not less than 99.5% and more preferably not less than 99.99% as the electrode material.

The above mentioned and other purposes of the invention can be accomplished by the method of this invention, which comprises immersing a pair of electrodes or a dipole electrode, at least the sensing portion thereof being composed of gold, which is 99.0%, preferably not less than 99.5% and more preferably not less than 99.99% in a reaction system examined and monitoring and analyzing the variation in electric potential or current due to a component which decreases with its consumption during the reaction.

Other purposes of this invention can be attained by providing an electrode which is applicable to the above mentioned method and which comprises a tube having a closed bottom and two gold members which are 99.0%, preferably not less than 99.5% and more preferably not less than 99.99%, passed through the closed bottom of the tube so that at least one extremity thereof is projected outside the tube and acts as the sensing portions, terminals disposed on the upper portion of the tube and metal elements electrically connecting the gold members with the terminals and having good conductivity.

BRIEF DESCRIPTION OF THE DRAWINGS

Hereinafter, the method and the electrode according to the present invention will be explained in more detail referring to the attached drawings in which.

DETAILED DESCRIPTION OF THE INVENTION

The method of this invention can effectively be applied to organic or inorganic reaction systems, in which oxidation-reduction reactions take part and to a certain precipitation reaction such as quantitative analysis of mirabilite as well as the exchange reaction in which active proton takes part (hereinafter the term "oxidation-reduction" is defined as including such exchange reaction). For example, zero-current potentiometric titration comprising measuring the potential change of the indicator electrode at the equivalence point and constant-current potentiometric titration comprising measuring the potential change under the condition such that the indicator electrode is polarized by applying a low constant current, as the potentiometric titration may be mentioned, while as the amperometric titration, constant-potential amperometric titration and dead stop titration techniques may be mentioned.

The method according to the present invention can be applied to, in particular, reaction systems in which a desired amount of titrant (one starting material) is gradually added to an examined reaction system containing another starting material and which cause variation of the electric potential or current due to the presence of an excess amount of the titrant, and thus an excellent result can be expected. However, the present invention is not restricted only to such reaction systems and it may also be applicable to determine the end points of various known volumetric titration systems. For instance, titrations in which the equilibrium potential is measured when the following oxidizing agents or reducing agents are used as the titrant: $Ce^{4+}$, $MnO_4^-$, $Cr_2O_7^{2-}$, $Fe(CN)_6^{3-}$, $IO_3^-$, $BrO_3^-$, $Cl\,O_C^-$ oxidizing agent, $Fe^{3+}$, $Ti^{3+}$, $Cr^{3+}$, $S_2O_3^{2-}$ (reducing agent). Furthermore, the method of this invention may be used to quantitatively analyze m-aminophenol, p-aminosalicylic acid, As (III), $N_2H_4$ or styrene using $KBrO_3$ as the titrant and hydrazine salts, hydroxylamine salts, sulfanilamide salts or cystine using $KIO_3$ as the titrant.

Figure 1:
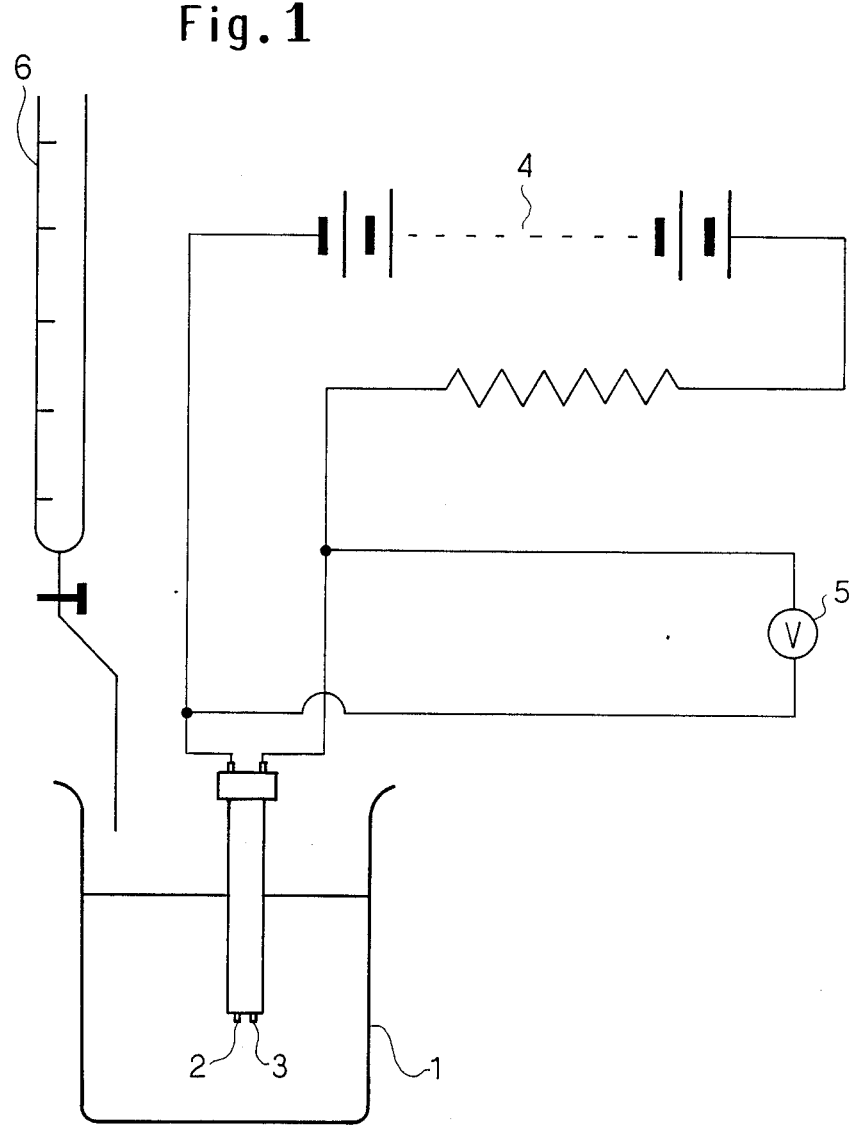
FIG. 1 is an illustrative diagram to explain the electrochemical method for determining the end point of reactions, according to the present invention.

The method of this invention can be carried out using an apparatus such as shown in FIG. 1 in which an example of the constant current potentiometric titration system is illustrated. The apparatus comprises a vessel 1 containing a solution to be analyzed, an electrode having sensing portions 2 and 3 of gold which is 99.0%, preferably not less than 99.5% and more preferably not less than 99.99% to detect the potential variation in proportion to the proceeding of the reaction, a direct current source 4 supplying a constant current to the electrodes (or the solution examined) and a potentiometer 5. In the system, a dipole gold electrode or a pair of electrodes having a sensing portion of gold which is 99.0%1, preferably not less than 99.5% and more preferably not less than 99.99% must be used and the stepwise addition of titrant is effected using, for instance, a burette 6.

According to the method of this invention, the end point and the reaction process of diazotization and azo coupling reactions, which are believed to be essential reactions in preparing dyestuffs and pigments as mentioned above, may be detected or examined effectively and therefore, it can be expected to quickly and directly obtain accurate information about end points and reaction processes without visual evaluation or indirect determination of such information. Moreover, the method according to the invention makes it possible to determine the end point of the reaction in which the reaction of an amino, a phenolic hydroxyl, an active methylene or a diazo group takes part, these groups sometimes showing an undetectablly low electrochemical response in a conventional polarographic titration.

As examples of organic compounds containing such amino groups, aliphatic amines, for instance, hydrazine, semicarbazide; aromatic amines or sulphonic derivatives thereof, for instance, 1-amino-8-hydroxynaphthalene-3, 6-disulphonic acid, aniline, toluidine, m-phenylene-diamine, toluylene diamine and chloride or nitro derivatives thereof, aminoacetoanilide, aminophenol, aminophenyl ether, aminosalicylic acid and sulphonic derivatives of these amines naphthylamine and sulphonic derivative thereof; the sulphonic derivative being, for example naphthionic acid, Laurent's acid, Freund's acid, Tobias' acid, Dahl's acid, Brönner's acid, amino-Crocein acid, C-acid, amino-G-acid, acetamino-Cleve's acid, Böniger's acid, 6-nitro-Böniger's acid may be mentioned.

Moreover, as examples of compounds including active methylene or diazo groups, p-sulfo-phenyl-3-methyl-5-pyrazolone, indole, keto-enol type compounds; or 1-diazo-2-naphthol-4-sulphonic acid, 1-diazo-2-naphthol-5-nitro-4-sulphonic acid, respectively may be mentioned.

As seen from the results of the following examples, the method of this invention can provide a high detection accuracy and response sensitivity even if the surface of the electrode used is contaminated with a certain component present in the reaction system examined or the surface thereof may not be contaminated with such component. Moreover, the method of this invention permits accurate end point determination of the reaction including at least two couplings such as diazotization or trisazotization which can't be detected by any conventional methods except for indirect methods.

Figure 2:
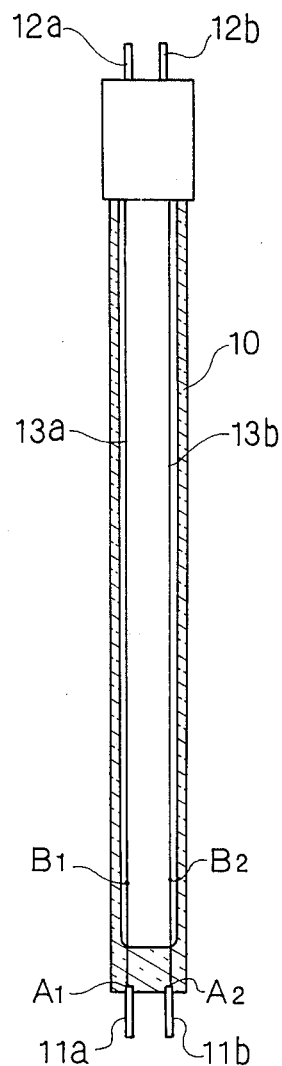
FIG. 2 shows a cross sectional view of a preferred embodiment of the dipole gold electrode according to the present invention.

Referring now to FIG. 2, a preferred embodiment of the electrode according to the invention is illustrated, which has a sensing portion of gold which is 99.0%, preferably not less than 99.5% and more preferably not less than 99.99%, and can be used in the method explained above. This is expected to provide excellent results. The electrode, which is a gold dipole type comprises a tube 10 having a closed bottom, gold members 11a and 11b acting as the sensing portions, these members being passed through the closed bottom of the tube 10 so that at least one extremity thereof protrudes outside the bottom of the tube 10, and terminals 12a and 12b disposed at the top portion of the tube 10, which are connected to the gold members 11a and 11b respectively. In this embodiment, the gold members which may be in the form of rods, wire or ribbon are directly connected to each terminal 12a or 12b. The gold members may, however be replaced by another conductive metal element or elements such as copper, aluminium, silver, and platinum in the form of wire, rod or ribbon. For instance, the gold members may be divided into two parts at points $A_1$, $A_2$. In this case, the protruded part must be gold and the other part 13a, 13b may be a metal element selected from the group consisting of copper, aluminium, silver and platinum. Furthermore, the parts 13a and 13b may be divided into two portions, for example, at points $B_1$ and $B_2$. These parts may be composed of any combination of different metals listed above including gold, such as platinum and copper. There is no restriction about the position of the points $A_1$, $A_2$, $B_1$ and $B_2$. The connection between the metals (for instance gold and platinum) at each point may be accomplished according to a known method such as silver soldering or engagement with a tubular metal such as platinum or copper.

Figure 3:
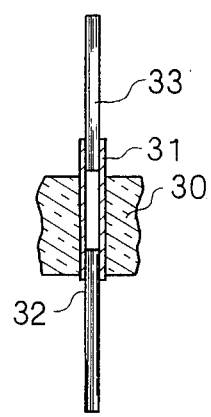
FIG. 3 shows a magnified cross sectional view of a part of another preferred embodiment of the dipole gold electrode according to the present invention.

As the material for the tube 10 which may effectively be used in the electrode according to the invention, glass and resin may be mentioned. The preferred resin is tetrafluoroethylene, since it is stable in acidic and alkaline mediums and inert to various kinds of reactants. In FIG. 3, there is shown a part of another preferred embodiment of the electrode of this invention. The electrode, in this embodiment, comprises a tube 30 having holes at its bottom, a platinum pipe 31 engaged with the hole, a gold rod 32 inserted into and engaged with the pipe 31 and having a protruded part outside the tube, and a metal rod 33 engaged with the pipe 31 at the opposite end. The rod 33 has a good electrical conductivity, and is connected to a terminal (not shown) through or without other conductive metal wire, rod or ribbon as already explained in FIG. 2.

Figure 4A:
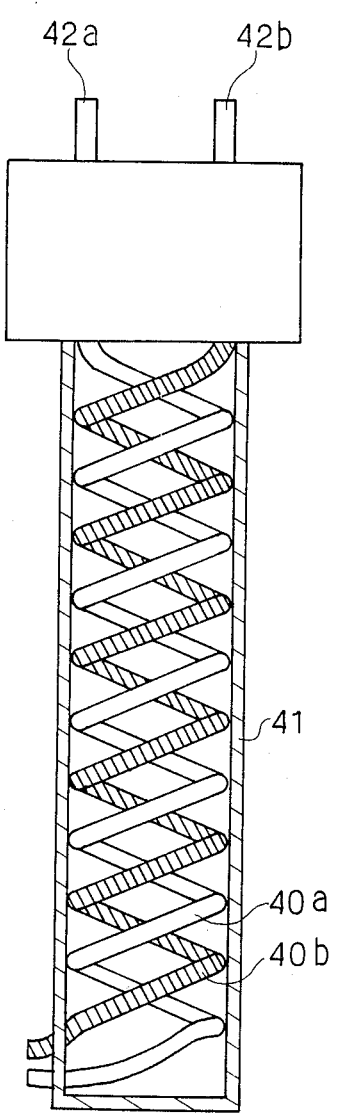
FIGS. 4a and 4b are illustrative diagrams of other embodiments of the electrode of this invention.
Figure 4B:
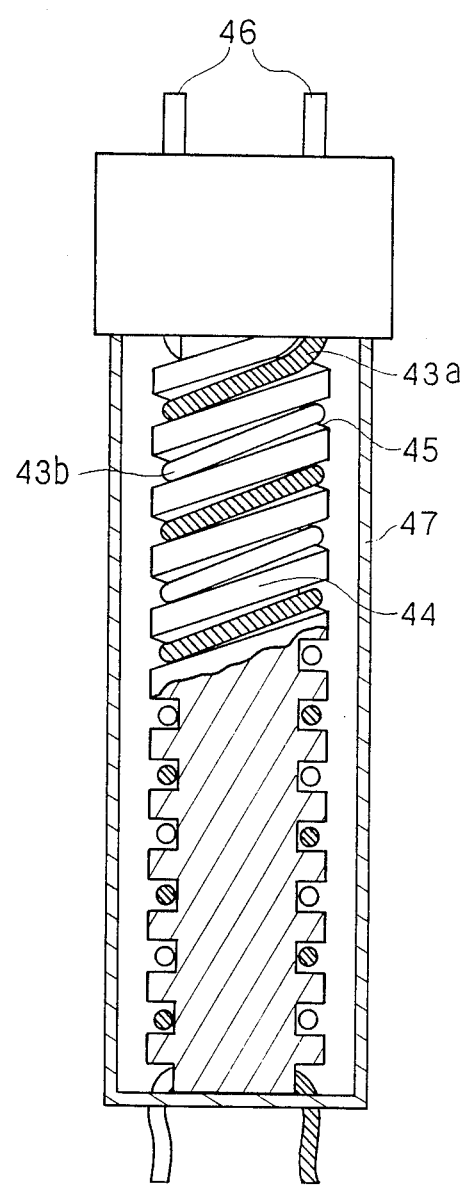

Further preferred embodiments of the electrode according to the present invention can be seen in FIGS. 4a and 4b. Referring to FIG. 4a, a pair of gold wires or rods 40a and 40b is in a helically wound state and contained in a tube 41 and one extremity of each helical wire projects outside the outer surface of the tube 41 and acts as the sensing portion, while the other extremity is connected to a terminal 42a or 42b. Turning now to FIG. 4a, another embodiment of the electrode is shown. In this electrode, a pair of gold wires 43a and 43b is helically wound to a core member 44 having a helical channel 45 in which the gold wires 43a, 43b are embedded. One extremity of the gold wire is connected to a terminal 46 and the other protrudes outside a tube 47 which receives the core 44 wound with the gold wires.

In these embodiments, a tube of glass or resin may be used and the part of the gold wire except for the sensing portion may also be exchanged with other metal wires, rods or ribbons having good electrical conductivity. Moreover, the gold wire may be wound to a core member having a smooth surface and further the wire may be embedded into the core member by heating it above its softening point and winding the wire to the core during heating. The core member may be prepared by a resin which is inert to the wire material preferably tetrafluoroethylene.

The present invention will be illustrated by the following non-limitative examples described with reference to the attached drawings, in which the effects attained according to the electrode or the method of this invention are clearly demonstrated. In the following examples, the apparatus as show in FIG. 1 is used, in which a dipole gold electrode according to the invention is disposed.

EXAMPLE 1

Determination of the End Point of Diazotization

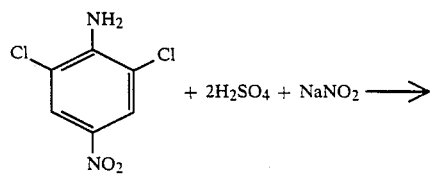

-continued

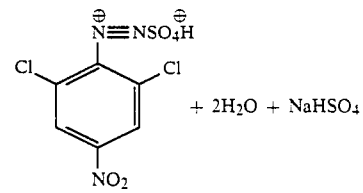

According to the above reaction equation, 2, 6-dichloro-4-nitroaniline diazonium salt was prepared and the end point thereof was determined by the constant-current polarization potentiometric titration technique (see FIG. 1) in which the titrant was sodium nitrite. The determination of the end point was carried out by introducing an aqueous solution containing 2, 6-dichloro-4-nitroaniline and sulfuric acid in the molar ratio of 1:2 into a vessel, immersing the dipole gold electrode in the solution, then applying a low constant current to the electrode and recording potential change with the gradual addition of the titrant which was added through a burette. Thus, the excess amount of sodium nitrite as the oxidizing agent was accurately determined from the observed variation in potential.

While, for the purpose of comparison, the same procedures as mentioned above were repeated, except that a pair of platinum electrodes was used instead of the gold electrodes of the invention and the end point was also determined from the potential variation examined.

Figures 5, 6:
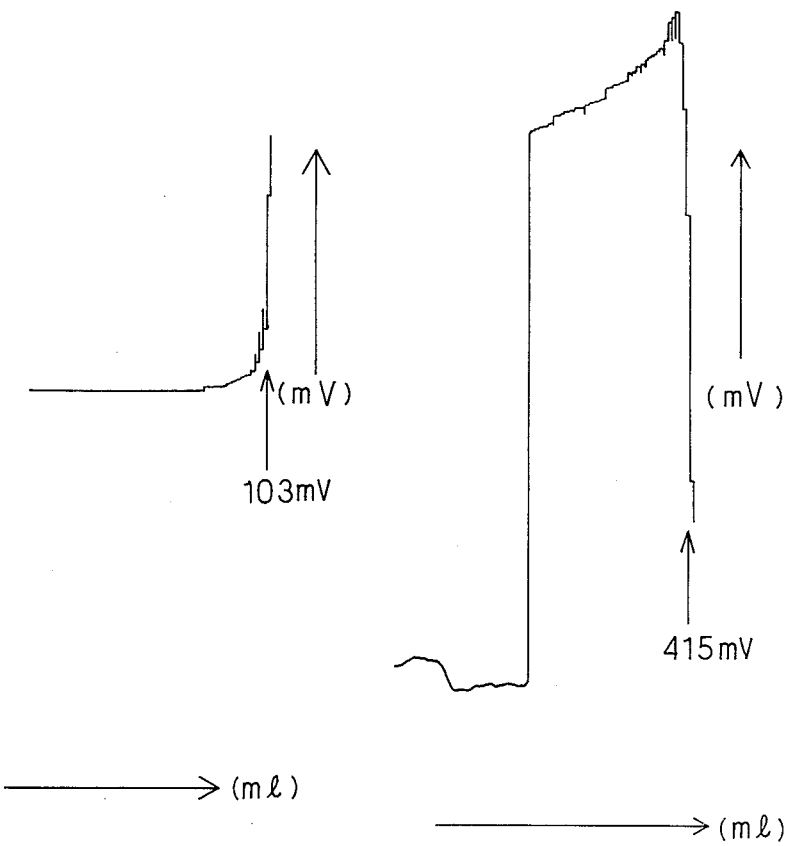
FIG. 5 shows the result (a chart) obtained when monitoring or detecting the end point and the process of diazotization reaction utilizing a conventional platinum electrode.
FIG. 6 shows a chart similar to FIG. 5 obtained using the gold electrode of this invention.

The results thus obtained were shown in FIGS. 5 and 6 respectively, as practically measured charts. The abscissa of the chart is the amount of sodium nitrite consumed during the reaction, while the ordinate thereof is the potential. FIG. 5 shows the result on the reference example in which a pair of platinum electrodes is used and the result shown in FIG. 6 is obtained according to the method of this invention using the dipole gold electrode.

From the results shown in FIGS. 5 and 6, the potential change at the equivalence point was observed to be 103 mV in the case of the reference example (see FIG. 5), while in the case of the present invention, the potential change is as high as 415 mV which is four times higher than that of the reference. Thus, the results of this example clearly demonstrate the effectiveness of the present invention.

EXAMPLE 2

Determination of the End Point of Azo Coupling Reaction

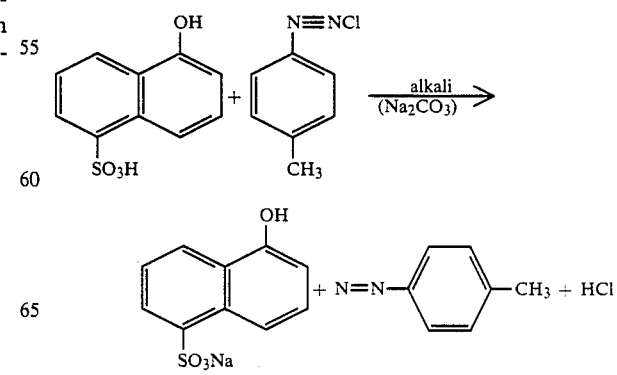

In this example, the end point of the azo coupling reaction between 1-naphthol-5-sulphonic acid and toluene diazonium salt according to the reaction equation as illustrated above was determined in accordance with the method of this invention. The same apparatus as in example 1 was used and the same procedures were repeated except that the titrant in the example was toluene diazonium salt and the reaction was carried out under alkaline condition ($Na_2CO_3$) and found that the excess amount of diazo component was estimated in a sufficient accuracy from the variation in potential observed. On the other hand, a comparative measurement was also carried out using a pair of platinum electrodes instead of the dipole gold electrode as in the example 1 and the results obtained are shown in FIGS. 7 and 8 in which the absciss is the amount of diazo component consumed during the above azo coupling reaction and the ordinate is the value of potential observed.

Figure 7:
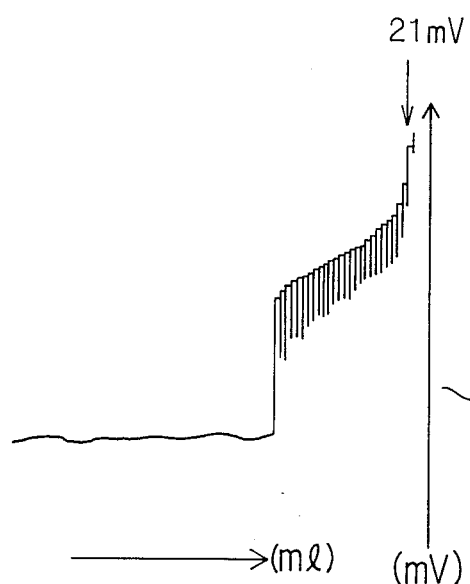
FIG. 7 shows the result (chart) obtained when the end point of a coupling reaction is detected by a conventional platinum electrode.
Figure 8:
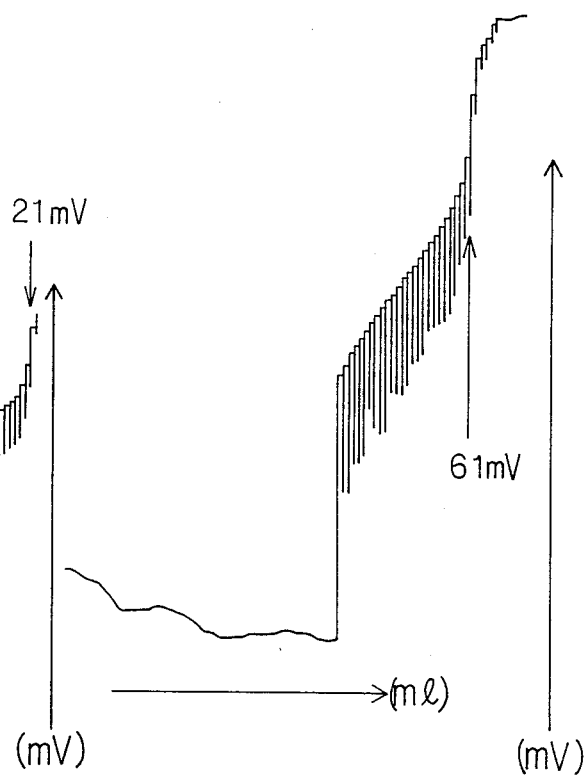
FIG. 8 shows the same result as shown in FIG. 7, obtained using the gold electrode according to the present invention.

According to the result shown in FIG. 7 corresponding to the comparative measurement, the potential change at the equivalence point was as low as 21 mV. While, the potential change in the measurement according to the invention (see FIG. 8) was 61 mV which is three times higher than that of the comparative measurement. Therefore, it is clear that the present invention is also effective to monitor or examine the processes and the end point of azo coupling reaction and the measurement sensitivity is extremely improved according to the method of this invention using the gold electrode.

Moreover, the measurement of the end point was repeated several times using a single electrode without replacing it during a series of measurements in order to determine the reproducibility and the change in sensitivity of the electrodes. The results obtained are listed in the following Table I:

TABLE I

| Electrode Used | Number of Repetitions | CV*(%) |
|---|---|---|
| Pt (Comparative measurement) | 6 | 1.48 |
| Au (Present Invention) | 6 | 0.40 |

*Coefficient of variation

From the results listed in Table I, it is observed that a stable potential variation is not obtained when the conventional platinum electrode is used, on the contrary the quite stable potential variation is observed in good reproducibility when the dipole gold electrode according to the invention is used.

EXAMPLE 3

Detection of the End Point of Azo Coupling Reaction (i) The Primary Coupling Reaction:

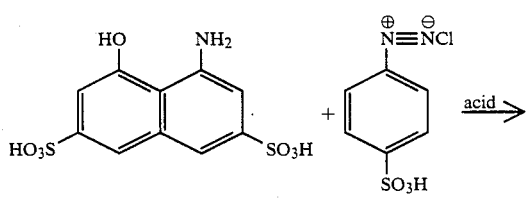

In this example, the method of this invention was carried out to determine the end point of the primary coupling reaction in which the monoazo compound disclosed in the above chemical equation is prepared by reacting 1-amino-8-naphthol-3, 6-disulphonic acid with diazonium salt of benzene sulphonic acid. The apparatus used and the procedures were the same as in the Example 1. The results observed are shown in FIGS. 9a to 9e.

Figure 9A:
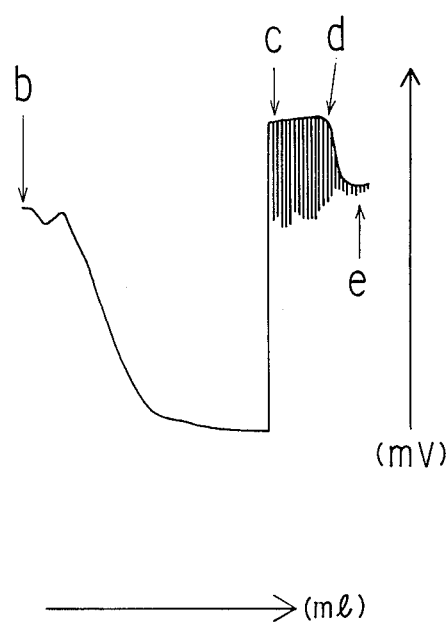
FIGS. 9a to 9e and FIGS. 10a to 10e show the results obtained when the primary and the secondary coupling reactions are examined using the gold electrode of this invention and the results of the high performance liquid chromatography (HPLC) measurements on samples collected at various stages during the reactions, respectively.
Figure 9B:
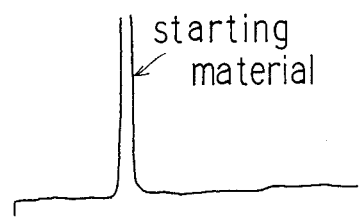

In FIG. 9a, the abscissa is the amount of diazo component consumed during the primary coupling reaction and the ordinate is the potential. During the reaction, a sample solution was collected at each one of the stages indicated by symbols b to e, and the samples were analyzed by high performance liquid chromatography (HPLC) and the results obtained were shown in FIGS. 9b to 9e respectively.

Figure 9C:
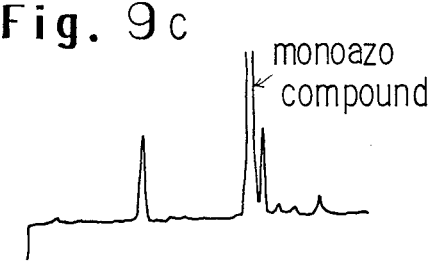
Figure 9D:
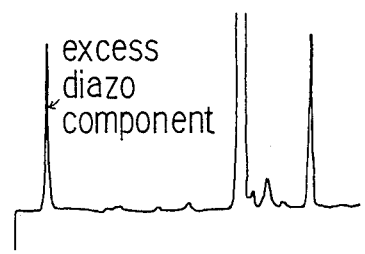
Figure 9E:
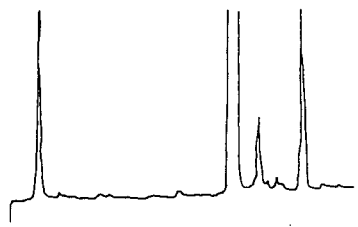

At the stage b (prior to titration), a sharp peak ascribed to 1-amino-8-naphthol-3, 6-disulphonic acid (starting material) was observed (see FIG. 9b) and at the stage c (during the coupling reaction) the height of the peak corresponding to the starting material was reduced, while a peak ascribed to the product (monoazo compound) appeared (see FIG. 9c). As shown in FIG. 9d, at the stage ascribed to d (equivalence point; showing a steep change in potential), the peak of the starting material (disulphonic acid) almost disappeared, the height of the peak corresponding to the monoazo compound (product) was largely increased and a new peak corresponding to excess diazo compound (titrant) appeared. Finally, at the stage e (excess diazo component being present), a high peak of monoazo compound and the peak of the excess titrant were observed (FIG. 9e).

The estimated potential change at the equivalence point was 20 mV in the case of the primary coupling reaction. Comparing the result obtained with that obtained according to the HPLC measurement, it was found that there was a small amount of diazo component at the equivalence point.

Thus, from the titration curve obtained, it was found that the end point could clearly be determined as the equivalence point in the titration curve.

(ii) The Secondary Coupling Reaction:

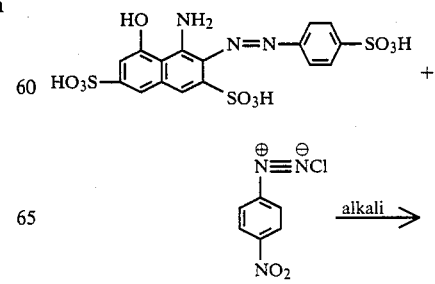

-continued

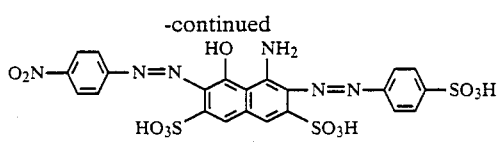

Figure 10:
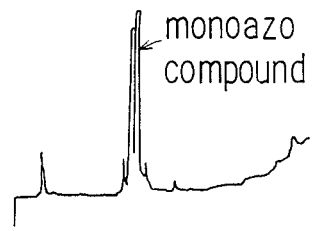
Figure 10:
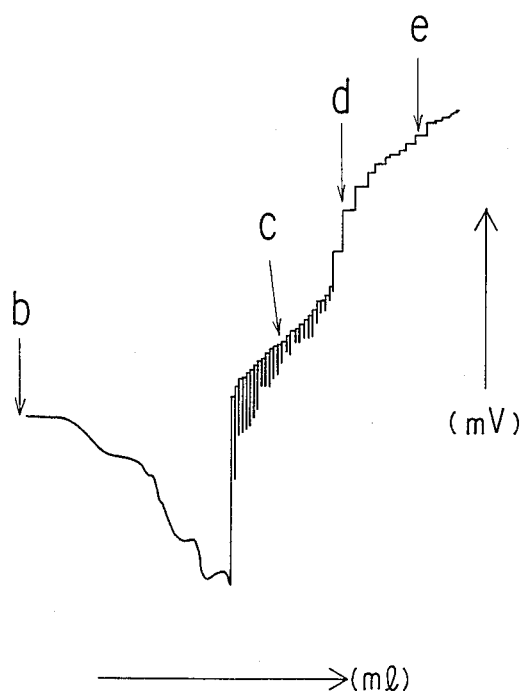
Figure 10:
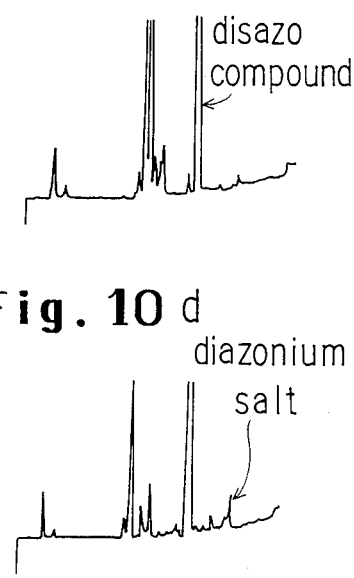
Figure 10:
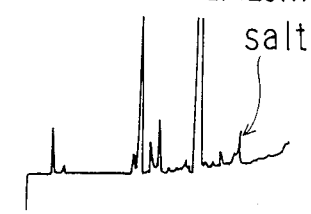
Figure 10:
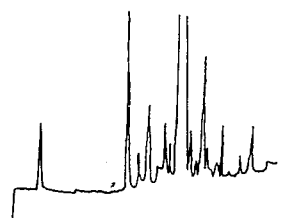

In this example, the method of this invention was applied to determine the end point of the secondary coupling reaction in which the diazo compound described in the above equation was prepared by reacting the monoazo compound obtained from the step (i) with diazonium salt of nitrobenzene under an alkaline condition. The same apparatus and procedures as in the step (i) are used and repeated. The resulting data were shown in FIGS. 10a to 10b. FIG. 10a is similar to FIG. 9a and shows a diagram in which the amount of diazo component (abscissa) was plotted against the potential value measured (ordinate). As in the case of the primary coupling reaction discussed before, a sample solution was collected at each stage indicated by symbols b to e (FIG. 10a) during the coupling reaction, thereafter the samples collected were analyzed according to the HPLC technique and the resulting charts are shown in FIGS. 10b to 10e respectively. In the secondary coupling reaction, there were obtained results identical to those shown in FIGS. 9b to 9e. In this case, the estimated potential change at the equivalence point was 15 mV. It is, thus, believed that the end point of the second coupling reaction can clearly be recognized as the equivalence point of the titration curve obtained.

In light of the above teachings various modifications and variations of the present invention are contemplated and will be apparent to those skilled in the art without departing from the spirit and scope of this invention. For instance in the method of this invention, a pair of monopole gold electrodes may be used instead of the dipole type gold electrode which is not referred to in the examples and identical good results can be expected.

What is claimed is:

1. An electrochemical method for detecting the end point of diazotization of azo coupling reactions accompanying an oxidation-reduction or precipitation reaction, which comprises the steps of: immersing an electrode having a sensing portion of gold which is not less than 99.0% in purity in the reaction system containing organic or inorganic compounds; and detecting and analyzing the electrical potential or current variation depending on the extent of the reaction.

2. An electrochemical method according to claim 1 wherein a pair of electrodes having a sensing portion of gold are used.

3. An electrochemical method according to claim 1 wherein the electrode used is a dipole gold electrode.

4. An electrochemical method according to claim 1 wherein the diazotization or azo coupling reaction includes a reactant selected from the group consisting of an organic compound having a phenolic hydroxyl, an active methylene or diazo group and aliphatic or aromatic amines.

5. An electrochemical method according to claim 1 wherein the azo coupling reaction is a primary azo coupling reaction or a secondary azo coupling reaction.

6. A method as set forth in claim 1, wherein said sensing portion of gold is not less than 99.5% in purity.

7. A method as set forth in claim 1, wherein said sensing portion of gold is not less than 99.99% in purity.

* * * * *